United States Patent [19]

Hayano et al.

[11] Patent Number: 5,072,128
[45] Date of Patent: Dec. 10, 1991

[54] DEFECT INSPECTING APPARATUS USING MULTIPLE COLOR LIGHT TO DETECT DEFECTS

[75] Inventors: Fuminori Hayano, Yokohama; Sunao Murata, Kanagawa, both of Japan

[73] Assignee: Nikon Corporation, Tokyo, Japan

[21] Appl. No.: 554,839

[22] Filed: Jul. 20, 1990

[30] Foreign Application Priority Data

Jul. 26, 1989 [JP] Japan .................................. 1-193764
Dec. 20, 1989 [JP] Japan .................................. 1-330163

[51] Int. Cl.⁵ .......................................... G01N 21/88
[52] U.S. Cl. .................................. 250/572; 250/226; 356/237
[58] Field of Search ............... 250/226, 562, 571, 572; 356/237, 239, 445–448; 209/582

[56] References Cited

U.S. PATENT DOCUMENTS

| 3,945,729 | 3/1976 | Rosen | 209/582 |
| 3,971,956 | 7/1976 | Jakeman et al. | 250/571 |
| 4,468,120 | 8/1984 | Tanimoto et al. | 356/237 |
| 4,669,875 | 6/1987 | Shiba et al. | 250/572 |
| 4,716,299 | 12/1987 | Tanaka et al. | 250/571 |
| 4,776,702 | 10/1988 | Yamaba | 250/226 |
| 4,831,274 | 5/1989 | Kohno et al. | 250/572 |
| 4,889,998 | 12/1989 | Hayano et al. | 250/563 |
| 4,966,457 | 10/1990 | Hayano et al. | 250/572 |

FOREIGN PATENT DOCUMENTS

63-186132 8/1988 Japan .
63-52696 10/1988 Japan .

Primary Examiner—David C. Nelms
Assistant Examiner—Stephone Allen
Attorney, Agent, or Firm—Shapiro and Shapiro

[57] ABSTRACT

A defect inspecting apparatus for discriminating one of two surfaces of a flat transparent object such as a pericle. The flat object is irradiated with a beam of light which is supplied from a light source and which is multiple-color light having predetermined wavelength ranges or white light of a broad band, scattered light from the defect is received by an optical element having wavelength selectivity, and scattered lights thereby separated with respect to the particular wavelength ranges are photoelectrically detected. The intensities of photoelectric signals thereby obtained are compared with each other.

14 Claims, 9 Drawing Sheets

DEFECT INSPECTING APPARATUS USING MULTIPLE COLOR LIGHT TO DETECT DEFECTS

BACKGROUND OF THE INVENTION

1. Field of the Invention

This invention relates to an apparatus for examining surfaces of a transparent flat object such as a glass member or a pericle and, more particularly, to an apparatus for detecting foreign particles attached to surfaces of such a flat object. More specifically, the present invention relates to an inspection apparatus capable of discriminating the positions of foreign particle detects with respect to obverse and reverse surfaces of the flat object.

2. Related Background Art

A technique for protecting a reticle (or a mask) used for projection exposure apparatus for manufacturing semiconductor devices is known which technique is based on covering the reticle with a pericle formed of a thin film of a high polymer such as nitrocellulose. The pericle is supported over the reticle by a support frame to cover the reticle while being spaced apart from the surface of the reticle by a certain distance, thereby preventing any foreign particles from attaching the reticle.

The pericle has a thickness of about 1 μm and a transmissivity of 90% or higher with respect to exposure illumination light. The thickness of the support frame is determined so that the stand-off of the pericle from the reticle surface is several millimeters, which is determined in consideration of the depth of focus of the projection optical system of the exposure apparatus on the reticle side.

If IC patterns are projected for exposure on a wafer by using a reticle and a pericle combined in this way, the image of a foreign particle on the reticle surface is transferred onto the wafer while being reduced according to the reduction ratio of the projection optical system, but the image of a foreign particle attached to the pericle is not resolved since it is defocused on the wafer surface. However, if the size of a particle on the pericle is greater than several ten microns, the image of this particle appears on the wafer as a defocused shadow. Accordingly, it is also necessary to check foreign particles attached to the pericle.

A type of inspection apparatus used for this purpose including the ones disclosed in Japanese Patent Publication No. 63-52696 and the one U.S. Pat. No. 4,716,299 is known in which a surface to be inspected is irradiated with a laser beam led at a small angle to this surface to form a stripe-like irradiation region on the inspected surface, and in which a one-dimensional array sensor is disposed in a position at which it can receive side scattered light among the scattered light from the irradiation region. However, according to this conventional technique, it is not possible to discriminate whether a foreign particle is attached to the obverse surface of the pericle (on the light source side) or to the reverse surface of the pericle (on the reticle side).

It is very important in terms of photolithography process to know whether a foreign particle attached to the pericle exists on the obverse side or on the reverse side. If the foreign particle is attached to the reverse surface, there is a risk of the foreign particle moving apart from the pericle and attaching to the reticle and, hence, a risk of occurrence of a defect in a shot on the exposure wafer effected by using this reticle. In such a situation, it is necessary to remove the pericle from the reticle together with the frame, to perform foreign particle removing operation for the reticle alone, and to replace the pericle with a new one.

It is therefore important to correctly know whether or not replacement with a new pericle is necessary before the exposure operation on the actual device.

Japanese Patent Laid-Open No. 63-186132 (corresponding to U.S. Pat. No. 4,889,998) discloses an apparatus for discriminating whether a foreign particle is attached to the obverse surface or the reverse surface of a pericle. This apparatus, however, requires a pair of light sources for drop shot illumination and oblique illumination.

U.S. Pat. No. 4,468,120 discloses an apparatus for discriminating whether a foreign particle is attached to the obverse surface or the reverse surface of a glass substrate. This apparatus requires a pair of photoelectric elements, i.e., a photoelectric element for receiving scattered light produced in a space on the obverse side of the substrate and another photoelectric element for receiving scattered light produced in a space on the reverse side of the substrate. Although the discrimination of the obverse or reverse surface to which a foreign particle is attached may be possible based on the same principle with respect to the pericle alone, it is not possible to inspect the pericle when the pericle is attached to the reticle, because the scattered light is shaded by patterns (chrome layer) on the reticle.

SUMMARY OF THE INVENTION

It is an object of the present invention to provide a defect inspecting apparatus capable of detecting whether any foreign particle is attached to a pericle or a thin glass plate, and capable of easily and correctly discriminating the surface on which the foreign particle is attached.

To this end, the present invention provides a defect inspecting apparatus capable of discriminating whether a defect such as a foreign particle is located on the obverse or reverse surface of a flat object based on irradiating the flat object with a beam of light which is supplied from a light source and which is multiple-color light having predetermined wavelength ranges or white light of a broad band, receiving scattered light from the defect by means of an optical element having wavelength selectivity (e.g., a dichroic mirrors, cold mirror, or a prism), photoelectrically detecting scattered separated with respect to the particular wavelength ranges, and comparing the intensities of photoelectric signals thereby obtained.

DESCRIPTION OF THE PREFERRED EMBODIMENTS

First, the principle of the present invention will be described below.

Figure 1:
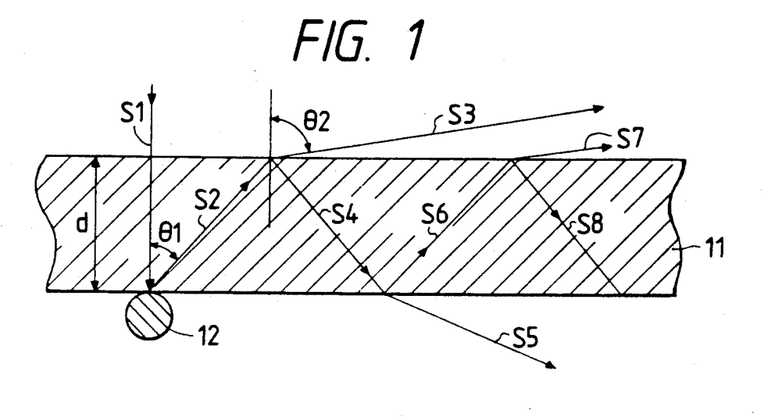
FIG. 1 is a diagram of the principle of the present invention.

FIG. 1 shows a state in which a foreign particle 12 is attached to the reverse surface of a pericle 11 (the inner surface of the pericle). The pericle 11 is irradiated with a beam S1 of white light or multiple-color light on the obverse side (on the side of the outer surface of the pericle) led perpendicularly to the pericle or at an angle close to the right angle.

The conclusion is as follows. In a case where scattered light from the foreign particle 12 is photoelectrically detected through the pericle 11 as shown in FIG. 1, the wavelength distribution of scattered light traveling to the photoelectric detector is different from that of the beam S1. In contrast, in a case where the foreign particle is attached to the inner surface of the pericle 11, scattered light from the foreign particle travels to the photoelectric detector while maintaining substantially the same wavelength distribution as the beam S1. It is therefore possible to discriminate the surface to which the foreign particle is attached by detecting the difference between the wavelength distributions of scattered light incident upon the light receiving system.

This effect will be described below in more detail. In the state shown in FIG. 1, scattered light S2 among the scattered light from the foreign particle returns to the outer surface by traveling at an angle of $\theta 1$ to the beam S1.

The scattered light S2 is separated into light S3 emerging from the outer surface of the pericle 11 and traveling to the light receiving system and light S4 directed to the inner surface by inner surface reflection. If the refractive index of the pericle 11 is n, the emergence angle $\theta 2$ of the light 3 is expressed by an equation:

$$\theta 2 = \sin^{-1}(n \cdot \sin \theta 1) \quad (1)$$

The light S4 is separated into light S5 and light S6 refracted at the inner surface of the pericle 11 and light S6 reflected by this surface, and the light S6 reflected on the inner surface is refracted and reflected at the outer surface of the pericle 11. Of the light S6, light S7 refracted at the outer surface of the pericle 11 travels to the light receiving system substantially parallel to the light S3. Accordingly, the emergence angle of the light S7 is also represented by $\theta 2$.

If the thickness of the pericle 11 is d, the phase difference $\delta$ between the light S3 and the light S7 is expressed by an equation:

$$\delta = \frac{4\pi \cdot n \cdot d \cdot \cos \theta 1}{\lambda} \quad (2)$$

The condition of the phase difference $\delta = 360°$, that is, the wavelength $\lambda m$ at which $\delta = 2m\pi$ (m: arbitrary integer) is $$\lambda m = \frac{2 \cdot n \cdot d \cdot \cos \theta 1}{m} \quad (3)$$

From equation (1), the angle $\theta 1$ is $$\theta 1 = \sin^{-1}\left[\frac{\sin \theta 2}{n}\right].$$

This equation is substituted in equation (3). Then the particular wavelength $\lambda m$ is expressed as $$\lambda m = \frac{2 \cdot n \cdot d \cdot \cos\left\{\sin^{-1}\left[\frac{\sin \theta 2}{n}\right]\right\}}{m} \quad (4)$$

Accordingly, if the angle between the optical axis of the scattered light receiving system and a normal on the pericle 11 is $\theta 2$, the lights S3 and S7 incident upon the scattered light receiving system have spectral characteristics including a peak at the wavelength $\lambda m$ and attenuation in the ranges of wavelengths about this wavelength. It is therefore possible to discriminate the surface to which the foreign particle is attached by examining the spectral characteristics of the scattered light from the foreign particle attached to the pericle.

As can be understood from the above-described principle, even under the fixed illumination condition, the particular wavelength $\lambda m$ at which a peak of the spectral characteristics of the scattered light is exhibited is changed if the angle between the optical axis of the scattered light receiving system and the pericle surface ($90° - \theta 2$) is suitably changed.

The particular wavelength $\lambda m$ is also changed if the optical axis of irradiation of the beam S1 is inclined from the perpendicular position on the pericle. However, if the inclination of the irradiation optical axis is increased, a difference occurs between the intensity of the beam irradiating the foreign particle located on the outer surface of the pericle and the intensity of the irradiating the foreign particle located on the inner surface of the pericle. Also, there is a possibility of a change in the spectral characteristics of the irradiation beam passing through the inner surface. It is therefore desirable to set the beam S1 irradiation axis close to the perpendicular position on the inspected surface.

For example, if the thickness d of the pericle is 1 μm; the refractive index n is 1.5; and the scattered light receiving angle $\theta 2$ is 80°, the particular wavelength m at which a peak is exhibited is $$\lambda m \approx 2.26/m \text{ (m: integer)}. \quad (5)$$

If the peak wavelength $\lambda m$ is within a range including a visible range and a near infrared range of wavelengths not longer than 1000 nm, there are $\lambda 5 = 452$ nm for $m = 5$, $\lambda 4 = 565$ nm for $m = 4$, and $\lambda 3 = 753$ nm for $m = 3$.

Similarly, if the scattered light receiving angle $\theta 2$ is 50°, the peak wavelength $\lambda m$ is $$\lambda m \approx 2.58/m \text{ (m: integer)}. \tag{6}$$

In the same wavelength range, $\lambda 6=430$ nm for $m=6$, $\lambda 5=516$ nm for $m=5$, $\lambda 4=645$ nm for $m=4$, and $\lambda 3=860$ nm for $m=3$.

It is assumed here that the wavelength range is set to 400 to 900 nm and is divided by 100 nm into ranges of 400 to 500 nm, 500 to 600 nm, 600 to 700 nm, 700 to 800 nm, and 800 to 900 nm. In the 400 to 500 nm wavelength range, $\lambda 5=452$ nm exists when $\theta 2=80°$, and $\lambda 6=430$ nm exists when $\theta 2=50°$. In the 500 to 600 nm wavelength range, $\lambda 4=565$ nm exists when $\theta 2=80°$, and $\lambda 5=516$ nm exists when $\theta 2=50°$. With respect to the 600 to 700 nm wavelength range, no integer m satisfying equation (5) exists in the case of the scattered light receiving system having the scattered light receiving angle of $\theta 2=80°$. That is, with respect to the 600 to 700 nm wavelength range, the scattered light from the foreign particle on the inner surface is not received.

In the case of the light receiving system of $\theta 2=50°$, $\lambda 4=645$ nm exists in the same wavelength range. A similar condition occurs with respect to the wavelength ranges of 700 to 800 nm and 800 to 900 nm. In the 700 to 800 nm wavelength range, $\lambda 3=753$ nm exists when $\theta 2=80°$, and no peak wavelength exists when $\theta 2=50°$. In the 800 to 900 nm wavelength range, no peak wavelength exists when $\theta 2$ is 80°, and $\lambda 3=860$ nm exists when $\theta 2$ is 50°.

As described above, in a case where the scattered light from a foreign particle located on the inner surface is received at different scattered light receiving angles ($\theta 2=80°$ and $\theta 2=50°$ in the above example), a phenomenon occurs in which the light can be received by one of the light receiving systems but cannot be received by the other according to the wavelength range.

In contrast, in the case of a foreign particle attached to the outer surface of the pericle, foreign particle scattered light is directly introduced into the light receiving system without passing through the pericle. The scattered light from the foreign particle located on the outer surface can therefore be received irrespective of the wavelength range by the two light receiving systems having different light receiving angles while maintaining the multiple-color light wavelength distribution characteristics.

Accordingly, in a case where scattered light from a foreign particle attached to the obverse or reverse surface of the pericle is received at two different light receiving angles with respect to certain wavelength ranges suitably divided, it is possible to discriminate whether the foreign particle is attached to the obverse or reverse surface of the pericle by comparing the two quantities of received light with respect to the same wavelength range.

In the above description, the two different light receiving angles at which the scattered light is detected by the light receiving systems are set to $\theta 2=80°$, 50°. However, it is essential to set the light receiving angles to the angles at which the discriminating performance is optimized based on equation (4). It is preferable to design the apparatus so that the light receiving angles can be adjusted to the optimum angles according to the wavelength characteristics of the utilized illumination light, the thickness of the pericle and so on.

Figure 2:
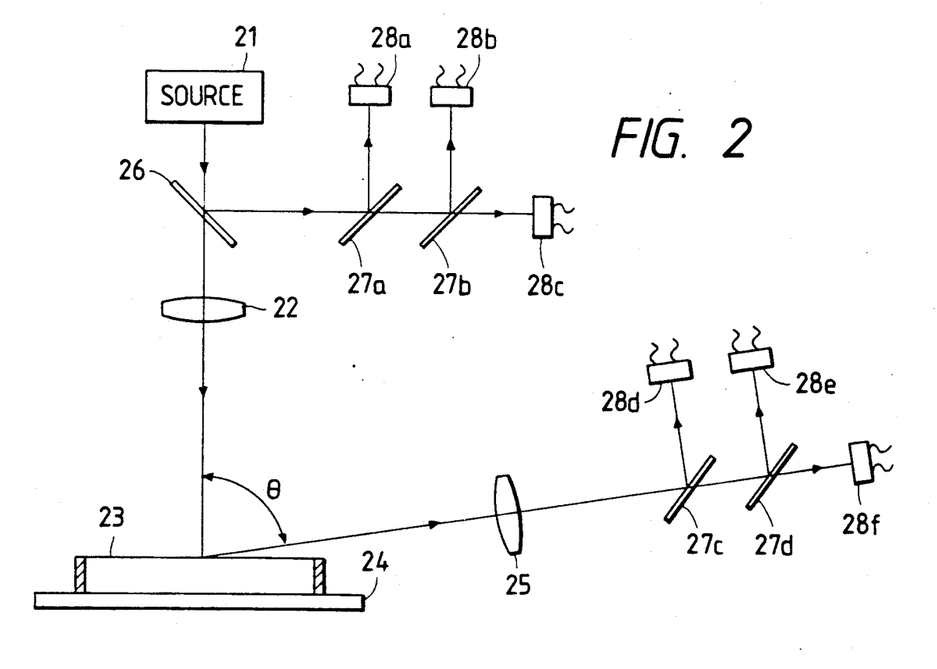
FIG. 2 is a diagram of the construction of an apparatus in accordance with a first embodiment of the present invention.

FIG. 2 shows the construction of a first embodiment of the present invention. A light source 21 is a white light source such as a tungsten lamp or halogen lamp. In this embodiment, illumination light having spectral characteristics of continuous wide-band wavelengths and wavelength characteristics of wavelengths extending to an infrared range of about 1000 nm.

A beam from the light source 21 is incident upon a condenser lens 22 through a beam splitter 26. The optical axis of the condenser lens 22 is perpendicular or approximately perpendicular to a surface of a pericle 23 disposed over a reticle 24. The condenser lens 22 condenses the illumination light to a local region (e.g., 1 mm square) on the pericle 23. It is preferable to provide an illumination field aperture at a position conjugate with that of the pericle 23 in the illumination optical system so that the illuminated region on the pericle has the shape of a rectangle, a fine slit or a circle accurately formed.

On the other hand, the scattered light receiving system includes a condenser lens 25 whose optical axis is inclined relative to a normal on the pericle 23 by an angle $\theta$, and through which the illuminated region on the pericle 23 is viewed. As described above, the angle $\theta$ is determined so that the particular wavelength $\lambda m$ corresponding to a peak of the spectral characteristics of scattered light can be suitably discriminated. Actually, it is set within a range of 45° to 85°.

A part of the scattered light from a foreign particle travels through the lens 25 and is separated into lights of two different wavelength ranges by a dichroic mirror 27c. The light of the wavelength range reflected by the dichroic mirror 27c is received by a photoelectric converter 28d, while the light of the wavelength range transmitted through the dichroic mirror 27c is further separated into lights of two different wavelength ranges by a dichroic mirror 27d. The light of the wavelength range reflected by the dichroic mirror 27d is received by a photoelectric converter 28e, and the light of the wavelength range transmitted through the dichroic mirror 27d is received by a photoelectric converter 28f.

For example, if the dichroic mirror 27c is a cold mirror (which reflects short-wavelength light but transmits long-wavelength light) having a boundary wavelength of 500 nm and if the dichroic mirror 27d is a cold mirror having a boundary wavelength of 600 nm, the level Vd of a signal output from the photoelectric converter 27d corresponds to the total quantity of light distributed in the range of wavelengths shorter than the wavelength of 500 nm among the scattered light from the foreign particle. Also, the level Ve of a signal output from the photoelectric converter 28e corresponds to the total quantity of light distributed in the range of wavelengths of 500 to photoelectric converter 28f corresponds to the total quantity of light distributed in the range of wavelengths longer than the wavelength of 600 nm.

Consequently, the two dichroic mirrors 27c and 27d serve as spectroscopic devices for dividing the wavelength distribution of the scattered light into three wavelength ranges.

A part of the illumination light reflected by the beam splitter 26 disposed in the illumination optical path is directed to the reference system described later in detail.

Figure 3:
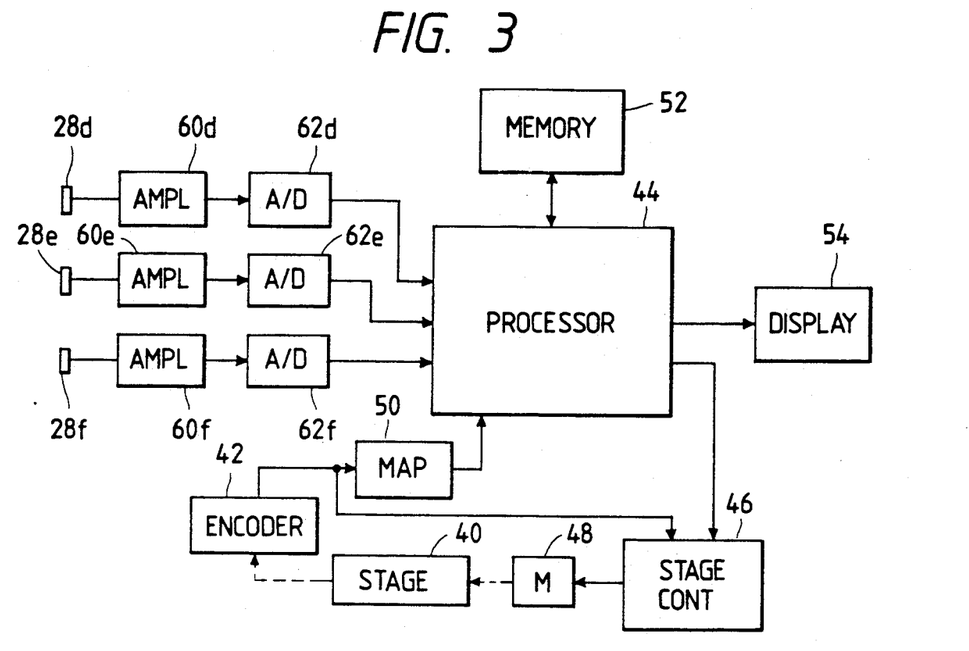
FIG. 3 is a block diagram of a signal processing system for the apparatus shown in FIG. 2.

FIG. 3 shows an example of a processing circuit for evaluating signals output from the photoelectric converters 28d, 28e and 28f. For ease of description of this embodiment, it is assumed that the reticle 24 on which the pericle 23 is mounted is placed on a two-dimensional scanning stage 40 to be moved in x- and y-directions relative to the irradiation beam. The movement of the scanning stage 40 is measured at a resolution finer than the size of the illuminated region by a coordinate position measuring device 42 such as an encoder.

A processor 44 outputs a movement command to a stage controller 46. The stage controller 46 receives a feedback signal supplied as position information from the encoder 42, and two-dimensionally moves the stage 40 by controlling a motor 48. The position information from the encoder 42 is input into a map circuit 50 to be converted into a coordinate position signal for displaying the position of the foreign particle on a 1 mm- or 5 mm-square map.

The signals output from the photoelectric converters 28d, 28e and 28f are amplified by amplifiers 60d, 60e and 60f, respectively and are converted into digital values by analog-digital converters 62d, 62e and 62f. The converted values are stored in a memory 52 through the processor 44.

A display 54 serves to display the results of inspection by using a color cathode-ray tube. The whole surface of the pericle is represented by a 1 mm- or 5 mm-square grid map. If the detected foreign particle is located on the outer surface, 1 mm- or 5 mm-square region corresponding to the position of this foreign particle is entirely colored, for example, green. If the particle is on the inner surface, the corresponding region is colored red. Character display of the size of the detected foreign particle is simultaneously effected by classifying the size of the particle into, for example, three ranks A, B and C and showing a character representing one of these ranks. Alternatively, the rank display may be effected by using gradations (luminance) of the coloring in green or red or by changing color tone slightly in a stepping manner.

For actual inspection, the stage 40 is moved one-dimensionally in the x-direction, is thereafter stepped in the y-direction by a distance corresponding to the size of the illuminated region, and is moved in the x-direction again. These movements are successively repeated.

Information on a standard ratios of the levels of photoelectric signals is previously stored in the memory 52. This standard ratio is determined so as to be approximately equal to the ratio Vd/Ve or Vf/Ve of the photoelectric signals Vd, Ve and Vf obtained if the foreign particle is attached to, for example, the inner surface. In this embodiment, the setting is such that the peak wavelength λm of the spectral characteristics exists in the range of wavelengths of the light received by the photoelectric converter 28e. Accordingly, the ratio Vd/Ve or Vf/Ve is approximately equal to the standard ratio if the foreign particle exists on the outer surface, or greatly differs from (or is greater than) the standard ratio if the foreign particle exists on the inner surface.

The processor 44 stores values output from the A/D converters 62d, 62e and 62f in the memory 52 in response to the sampling command issued from the map circuit 50 each time the stage 42 is moved by, for example, 1 mm.

After the scanning of the stage 40 has been completed, the processor 44 reads out inspection data items Vd, Ve and Vf with respect to the scanning positions (sampling positions), calculates the ratio Vd/Ve or Vf/Ve, compares the calculated ratio with the standard ratio to discriminate the surface to which the foreign particle is attached. The processor 44 displays the result of this discrimination through the display 54.

Also, the processor 52 ranks the foreign particle size on the basis of the photoelectric signal levels, and displays the results of this ranking.

In this embodiment, the light received by the photoelectric converter 28e is intensified by a phase shift of 2mπ, as described above with reference to FIG. 1, and it does not always represent the light quantity level in accordance with the foreign particle size. The foreign particle size can be determined by evaluating the signal levels Ve and Vf supplied from the other photoelectric converters 28d and 28f.

Referring again to FIG. 2, the diverging illumination light from the beam splitter 26 is divided into two wavelength ranges by a dichroic mirror 27a, and the light passing through this mirror is further divided into two wavelength ranges by a dichroic mirror 27b. The dichroic mirror 27a has the same wavelength selecting characteristics as the dichroic mirror 27d. Accordingly, a photoelectric converter 28a receives the total quantity of component light having wavelengths shorter than, for example, 500 nm, a photoelectric converter 28b receives the total quantity of component light having wavelengths in an intermediate wavelength range of 500 to 600 nm, and a photoelectric converter 28c receives the total quantity of component light having wavelengths longer than 600 nm.

Thus, the while illumination light can be separated based on the same characteristics as the spectroscopic means in the scattered light receiving system to form a reference signal with respect to each wavelength range, and the signals Vd, Ve and Vf of the light receiving system can be standardized by using the reference signals. More specifically, the standardization is effected by a processing circuit having a divider such as that shown in FIG. 4. In this case, dividing operation is performed in an analog manner but it may be performed based on a program of the processor.

Figure 4:
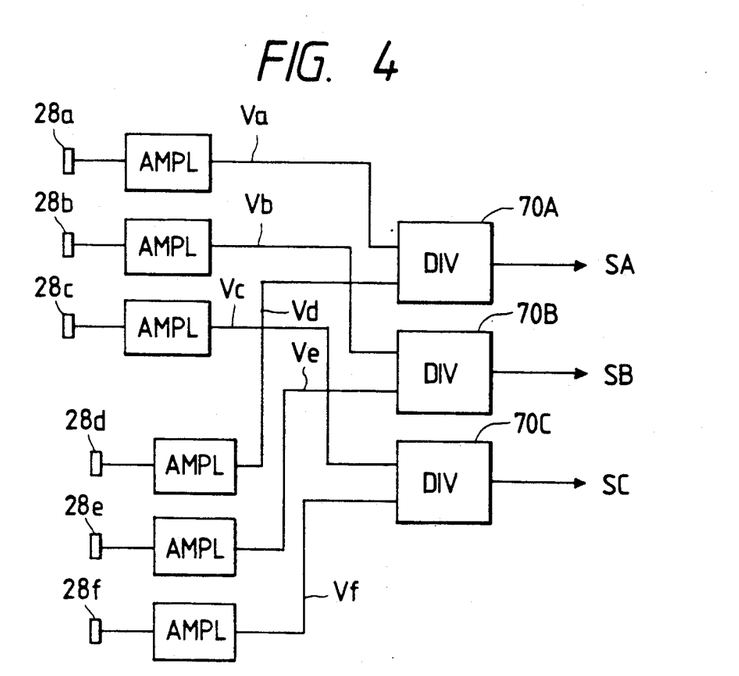
FIG. 4 is a block diagram of an example of a modification of the signal processing system.

The signal Va output from the photoelectric converter 28a and amplified and the signal Vd output from the photoelectric converter 28d and amplified are respectively input into a divider 70A, and the divider 70A outputs SA=Va/Vd. Similarly, a divider 70B produces an output SB =Vb/Ve based on the signal Vb from the photoelectric converter 28b and the signal Ve from the photoelectric converter 28e, and a divider 70C produces an output SC=Vc/Vf based on the signal Vc from the photoelectric converter 28c and the signal Vf from the photoelectric converter 28f.

The circuit shown in FIG. 4 is provided in place of the elements 28d to 28f and 60d to 60f. The outputs SA, SB and SC are input into the processor 44 shown in FIG. 3 through the A/D converters 62d to 62f and are stored in the memory 52.

In the case of scattered light from a foreign particle on the inner surface of the pericle, the signal levels Vd and Vf are smaller than the signal level Ve. The processor 44 compares the outputs SA, SB and SC, and determines that the foreign particle is located on the outer surface of the pericle (on the light receiving system side) if SA≈SB≈SC, or determines that the foreign particle is located on the inner surface if SA>SB<SC. It is thus possible to discriminate the surface to which the foreign particle is attached by evaluating the relationship between the levels of the standardized output values SA, SB and SC.

This decision circuit can also be formed of analog comparators, logic ICs and so on in a discrete manner.

Figure 5:
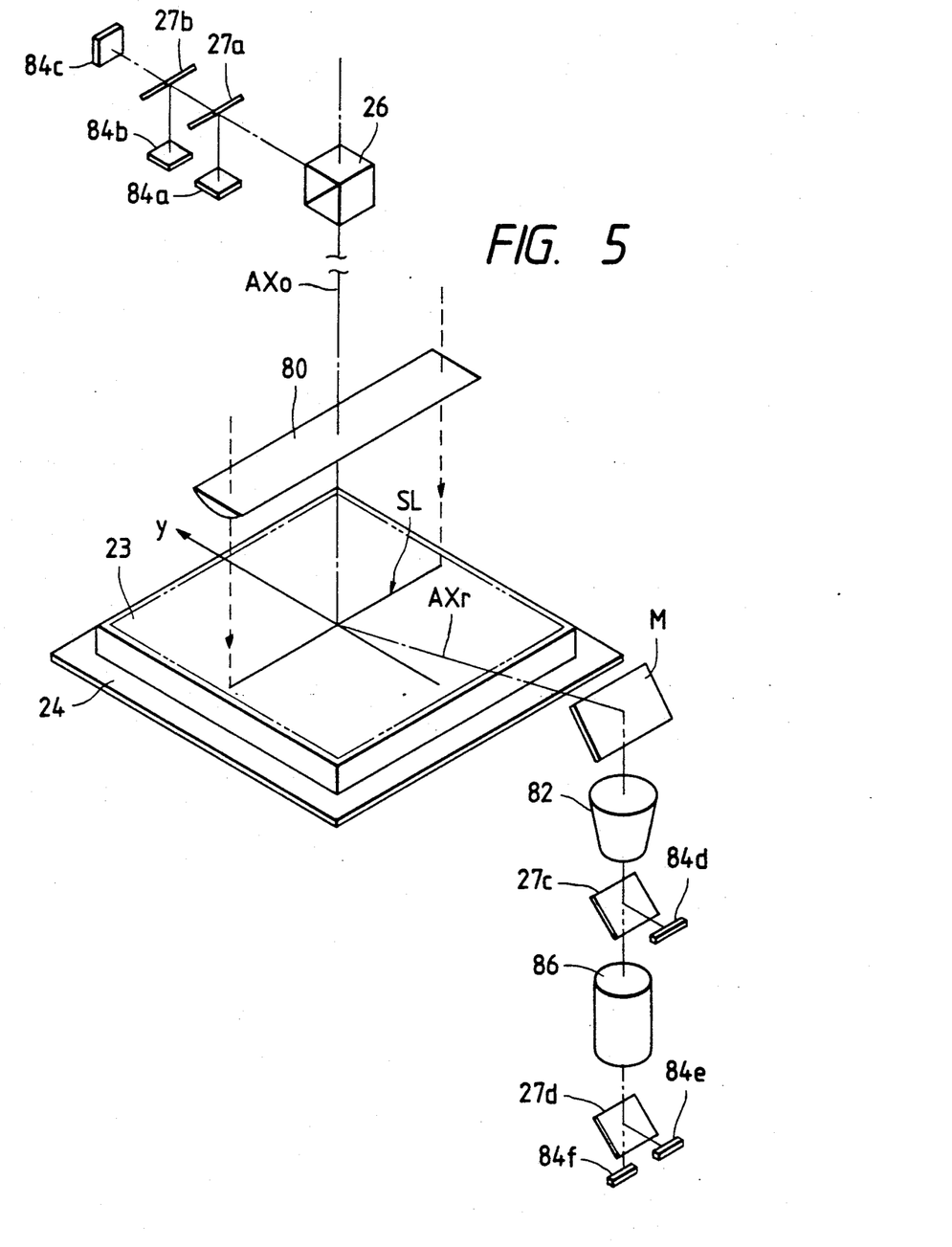
FIG. 5 is a perspective view of the construction of an apparatus in accordance with a second embodiment of the present invention.

FIG. 5 shows the construction of a second embodiment of the present invention.

The illumination optical system is provided with a cylindrical lens or toric lens 80 having a base line perpendicular to the y-direction. The optical axis AXo of the cylindrical lens 80 is perpendicular or approximately perpendicular to a pericle 23. White illumination light condensed by the cylindrical lens 80 is emitted to form a slit-like illumination light S1 extending in the x-direction on the pericle 23. A reticle 24 on which the pericle 23 is mounted is moved in the y-direction at a constant speed by a one-dimensional slider (not shown) or the like. The illumination light S1 has a length approximately equal to the wide of the pericle 23 in the x-direction.

On the other hand, the scattered light receiving system is formed of a mirror M, an imaging optical system 82, a dichroic mirror 27c, a relay system 86, a dichroic mirror 27d, and three one-dimensional imaging elements (such as CCDs) 84d, 84e and 84f. These components are disposed along an optical axis AXr. The optical axis AXr of the imaging optical system 82 is bent by the mirror M to set at a predetermined angle (about 5° to 20°) to the surface of the pericle 23. The imaging optical system 82 forms on the imaging element 84d an image of the region illuminated with the illumination light S1 reflected by the mirror M. At this time, scattered light from the illuminated region is reflected by the dichroic mirror 27c, and a dark image of the foreign particle is formed on the imaging element 84d by, for example, light having components of short wavelengths not longer than 500 nm. The image formed by the imaging optical system 82 is relayed at a substantially equal magnification by the relay system 86, and is divided into the range of wavelengths of 500 to 600 nm and the range of wavelengths longer than 600 nm by the dichroic mirror 27d. The separated lights are imaged on the one-dimensional imaging elements 84e and 84f.

Consequently, a dark image of the foreign particle is formed on the one-dimensional imaging element 84e from intermediate wavelength components (500 to 600 nm) in the slit-like illuminated region, while a dark image of the foreign particle is formed on the one-dimensional imaging element 84f from long wavelength components (longer than 600 nm) in the illuminated region.

The foreign particle position measurement resolution in the longitudinal direction of the illuminated region is determined by the number of pixels of each of the one-dimensional imaging elements 84d, 84e and 84f. For example, if the length of the illumination light S1 in the x-direction on the pericle is about 80 mm; the number of pixels of each one-dimensional imaging element is 512; and the number of effective pixels is 400 (an pericle frame image is formed for two 56 pixels at each side), a resolution of 200 μm on the pericle per pixel is obtained.

The reference optical system is formed in the same manner as that shown in FIG. 2. A part of the illumination light is separated by a beam splitter 26, and is divided into three wavelength ranges by the dichroic mirrors 27a and 27b, and photoelectric elements 84a, 84b and 84c receive lights having the respective wavelength ranges.

The processing circuit is constructed to effect standardization by using a divider in the same manner as the apparatus shown in FIG. 2.

Figure 6A:
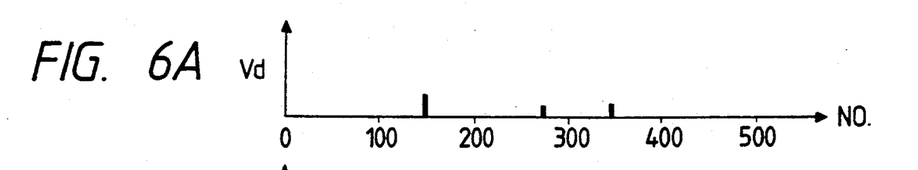
FIGS. 6A, 6B and 6C are graphs of signal levels obtained by photoelectric detection.
Figure 6B:
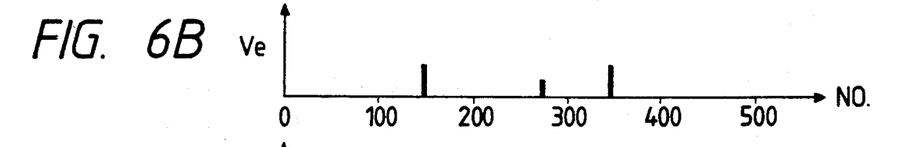
Figure 6C:
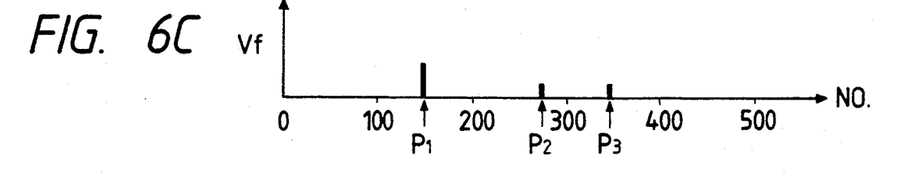

FIGS. 6A, 6B and 6C show examples of waveforms of image signals output from the imaging elements 84a, 84b and 84c for one line. In FIGS. 6A, 6B and 6C, the coordinates represent pixel signal levels Vd, Ve, and Vf and the abscissa represent pixel array numbers. The one line reading cycle and the speed at which the reticle 24 is moved in the y-direction are synchronized to maintain a certain relationship. In this example, an image signal for one line is obtained each time the reticle is moved by a distance corresponding to the width of the illumination light S1 in the y-direction.

At pixel positions P1, P2 and P3, signal levels higher than a certain level are obtained. At the position P1, each of the three signal levels Vd, Ve and Vf is large and the ratios Va/Vd, Vb/Ve and Vc/Vf are approximately equal after standardization. It is therefore determined that the foreign particle corresponding to the position Pl is located on the outer surface. At the position P2, each of Vd, Ve and Vf is small and the ratios Va/Vd, Vb/Ve and Vc/Vf are approximately equal after standardization. It is therefore determined that the foreign particle corresponding to the position P2 also located on the outer surface. Also, the result of signal level comparison shows that the foreign particle corresponding to the position Pl is greater than that corresponding to the position P2.

At the position P3, the level Ve is substantially greater than Vd and Vf. Accordingly, as a result of comparison of the ratios Va/Vd, Vb/Ve and Vc/Vf, the ratio Vb/Ve is different from the others. It is thereby found that the foreign particle corresponding to the position P3 is located on the inner surface.

Preferably, in this embodiment, the illumination distribution of the illumination light S1 in the longitudinal direction is uniform. If the desired uniformity cannot be achieved, the levels of the image signals may be corrected with respect to each pixel of or a plurality of pixels in a certain section based data on illumination distribution previously obtained. Also, standardization may be effected by using the corrected signal levels, and relationship between the standardized ratios may be evaluated.

Figure 7:
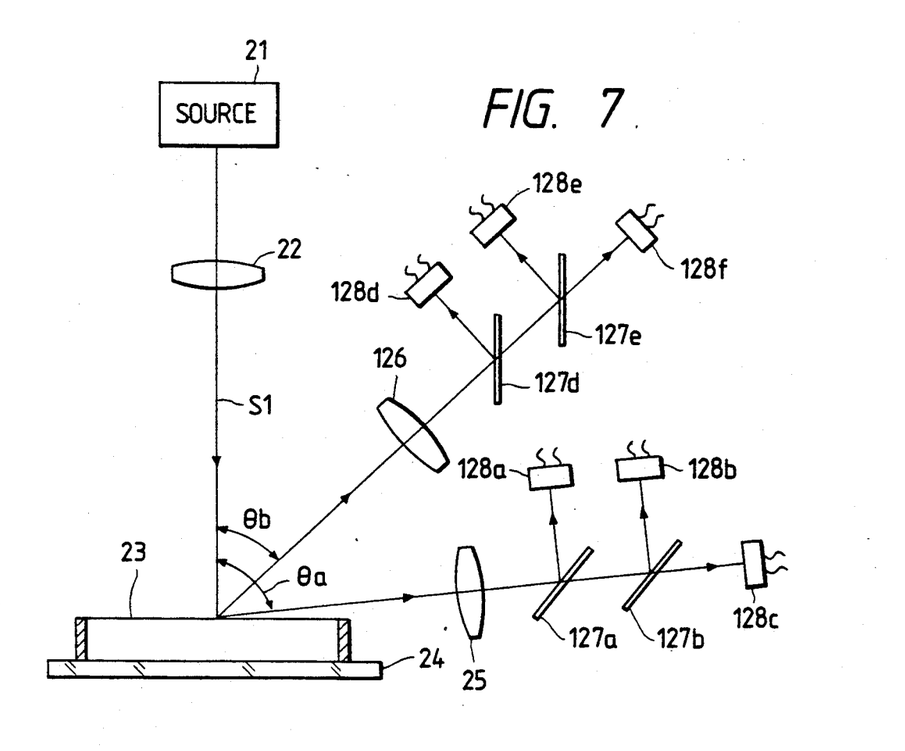
FIG. 7 is a diagram of the construction of an apparatus in accordance with a second embodiment of the present invention.

FIG. 7 shows the construction of a third embodiment of the present invention. Components corresponding or identical to those shown in FIG. 2 are indicated by the same reference characters and the description for them will not be repeated.

A pericle is irradiated with a beam S1 which is perpendicular or approximately perpendicular to the pericle surface. A first light receiving system constructed in the same manner as the light receiving system shown in FIG. 2 includes a condenser lens 25 inclined by and angle θa (e.g., 80°) relative to the normal on the pericle, dichroic mirrors 127a and 127b, and photoelectric converters 128a, 128b and 128c.

The second light receiving system includes a condenser lens 126 whose optical axis is inclined relative to a normal on the pericle by an angle θb (θb < θa). The angle θb is set to, for example, 50°. A part of the scattered light from a foreign particle travels through the lens 126, and the light of the wavelength range reflected by a dichroic mirror 27e is received by a photoelectric converter 28g. The light of the wavelength range transmitted through the mirror 27e and reflected by a dichroic mirror 27f is received by a photoelectric converter 28h, and the light of the wavelength range transmitted through the dichroic mirror 27f is received by a photoelectric converter 28i.

The dichroic mirrors 127a and 127b of the first light receiving system and the dichroic mirrors 127d and 127e of the second light receiving system have equal wavelength selectivity. For example, each of the dichroic mirrors 127a and 127b is a cold mirror (which reflects short-wavelength light but transmits long-wavelength light) having a boundary wavelength of 700 nm, and each of the dichroic mirrors 127d and 127e is a cold mirror having a boundary wavelength of 800 nm. The wavelength range of the illumination light S1 is previously limited to a range of 600 to 900 nm by a suitable filter.

The levels VA and VD of signals output from the photoelectric converters 128a and 128d correspond to the total quantity of light distributed in the range of wavelengths of 600 to 700 nm among the scattered light from the foreign particle. Also, the levels VB and VE of signals output from the photoelectric converters 128b and 128e correspond to the total quantity of light distributed in the range of wavelengths of 700 to 800 nm, and the levels VC and VF of signals output from the photoelectric converters 128c and 128f correspond to the total quantity of light distributed in the range of wavelengths of 800 to 900 nm.

Figure 8:
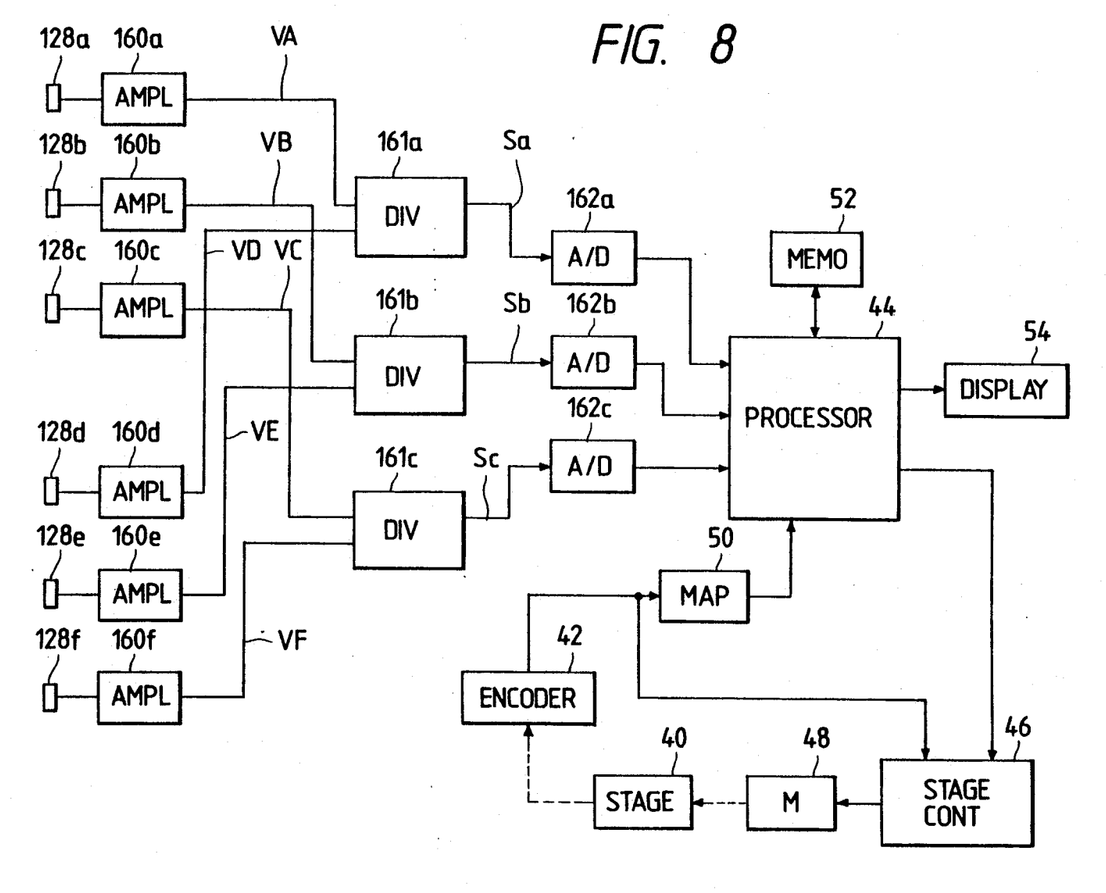
FIG. 8 is a block diagram of a signal processing system for the apparatus shown in FIG. 7.

FIG. 8 shows an example of a processing circuit for evaluating signals output from the photoelectric converters 128a, 128b, 128c, 128d, 128e and 128f which receive scattered light with respect to the particular wavelength ranges. The reticle on which the pericle is mounted is placed on a two-dimensional scanning stage 40. The movement of the scanning stage 40 is measured at a resolution finer than the size of the illuminated region by an encoder 42. A processor 44 outputs a movement command to a stage controller 46. The stage controller 46 receives a feedback signal supplied as position information from the encoder 42, and two-dimensionally moves the stage 40 by controlling a motor 48. The position information from the encoder 42 is input into a map circuit 50 which converts the information on the position of the foreign particle so that the position of the foreign particle can be displayed on a 1 mm- or 5 mm-square map.

The levels of the signal output from the photoelectric converters 128a to 128f are amplified by amplifiers 160a, 160b, 160c, 160d, 160e and 160f and are thereafter input into dividers 161a, 161b and 161c. These dividers operate in an analog manner. However, the dividing operation may be performed based on a program of the processor.

Each of the dividers 161a to 161c effects dividing using the values output from the photoelectric converters receiving light of the same wavelength range. That is, with respect to the scattered light having wavelengths of 600 to 700 nm, the signal VA from the photoelectric converter 128a and the amplifier 160a and the signal VD from the photoelectric converter 128d and the amplifier 160d are input into the divider 161a, and the divider 161a outputs the ratio Sa=VA/VD of these values.

Similarly, with respect to the scattered light having wavelengths of 700 to 800 nm, the signal VB from the photoelectric converter 128b and the amplifier 160b and the signal VE from the photoelectric converter 128e and the amplifier 160e are input into the divider 161b for calculation of the ratio Sb=VB/VE. With respect to the scattered light having wavelengths of 800 to 900 nm, the signal VC from the photoelectric converter 128c and the amplifier 160c and the signal VF from the photoelectric converter 128f and the amplifier 160f are input into the divider 161c for calculation of the ratio Sc=VC/VF. The division outputs Sa, Sb and Sc from these dividers are converted into digital values by analog-digital converters 162a, 162b and 162c, and the converted digital values are stored in a memory 52 through the processor 44.

A display 54 serves to display the results of inspection by using a color cathode-ray tube, as in the case of the first embodiment. That is, if the detected foreign particle is located on the outer surface, the corresponding position is colored, for example, green. If the particle is on the inner surface, the corresponding position is colored red. Character display for indicating the size of the detected foreign particle is also effected.

Figure 9A:
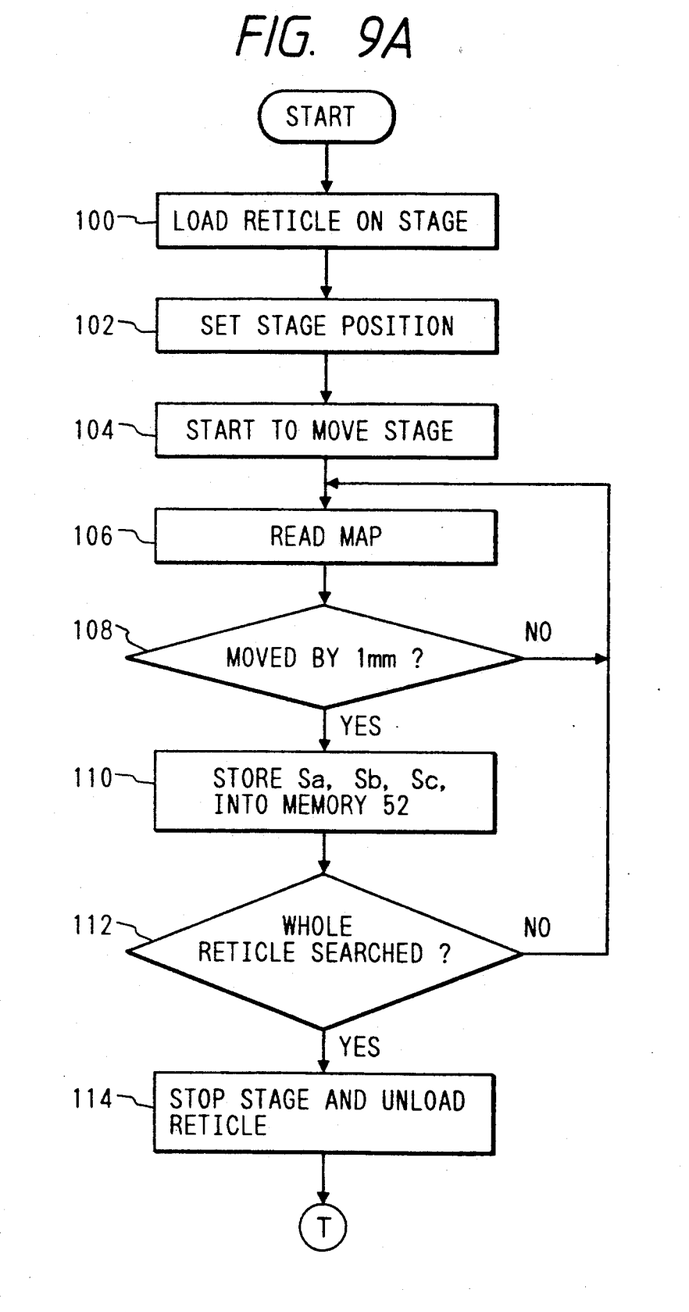
FIGS. 9A and 9B are flow charts of the operation of the third embodiment.
Figure 9B:
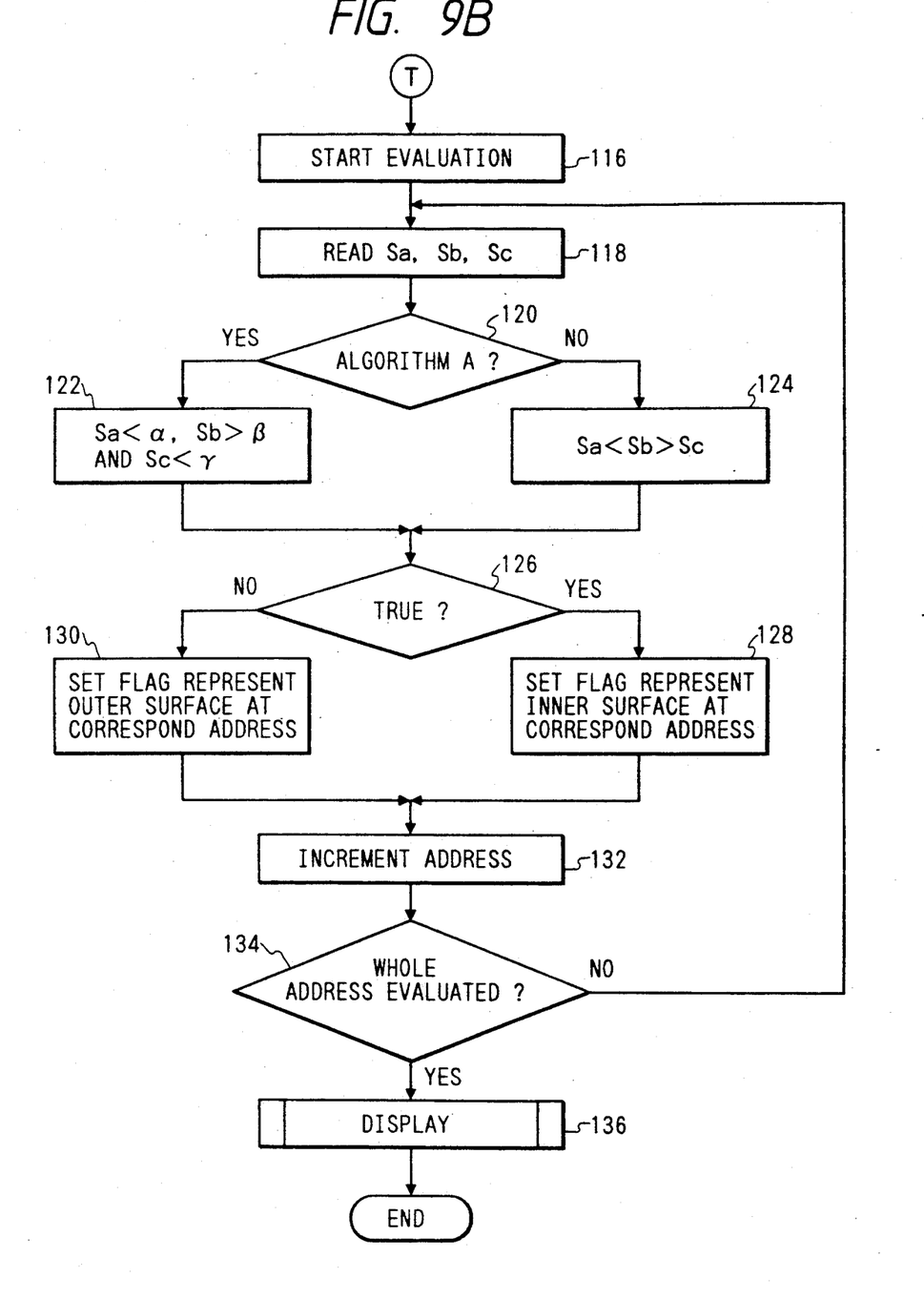

For actual inspection, as shown in detail as steps 100 to 136 of FIGS. 9A and 9B, the stage 40 is moved one-dimensionally in the x-direction, is thereafter stepped in the y-direction by a distance corresponding to the size of the illuminated region, and is moved in the x-direction again (steps 100 to 104). These movements are successively repeated.

The processor 44 stores values output from the A/D converters 162a, 162b and 162c in the memory 52 in response to the sampling command issued from the map circuit 50 each time the stage 40 is moved by, for example, 1 mm (steps 106 to 110). After the whole of the pericle has been completely searched, the processor 44 reads inspection data items Sa, Sb and Sc out of the memory 52 (steps 116 and 118).

Constants $\alpha$, $\beta$ and $\gamma$ which represent the ratios previously determined by, for example, experiment with respect to the wavelength ranges are stored in the memory 52. In this embodiment, the scattered light from a foreign particle located on the inner surface is detected by the photoelectric converter 128d of the second light receiving system alone with respect to the 600 to 700 nm wavelength range, and is not detected by the photoelectric converter 128a of the first receiving system. The ratio Sa (=VA/VD) is therefore smaller than $\alpha$, i.e., Sa<$\alpha$. Similarly, scattered light of the 700 to 800 nm wavelength range among the scattered light on the inner surface is detected by the photoelectric converter 128b of the first receiving system while being hardly received by the photoelectric converter 128e of the second light receiving system, and scattered light of the 800 to 900 nm wavelength range is detected by the photoelectric converter 128f of the second receiving system but is not received by the photoelectric converter 128c of the first light receiving system. Sb (=VB/VE)>$\beta$ and Sc(VC/VF)<$\gamma$ are therefore established.

It is determined that the foreign particle is located on the inner surface if Sa<$\alpha$, Sb>$\beta$ and Sc (VC/VF)<$\gamma$ (algorism A) are simultaneously satisfied, or that the foreign particle is located to the outer surface if these logical formulae are not satisfied (steps 120, 122, 126). Alternatively, the use of another logical formula is effective. That is, the three values Sa, Sb and Sc are compared with each other, and it is determined that the foreign particle is located on the inner surface if Sa<Sb>Sc (algorism B), or that the foreign particle is located on the outer surface if this inequality is not established (steps 120, 124, 126).

The processor 44 successively operates for the determination steps based on the information on each map position read out of the memory 52 (steps 128, 130, 132, 134) and displays the results of determination on the display 54 (step 136). The processor 44 also ranks the foreign particle size on the basis of the photoelectric signal levels, and displays the results of this ranking on the display 54. The photoelectric signal levels VA, VB, VC, VD, VE and VF are input into the processor 44 from the amplifiers 160a to 160f via unillustrated lines and are ranked by the processor 44 according to the particle size based on, for example, the maximum of the photoelectric signal levels.

In the receiving system having the larger angle to the pericle surface, the scattered light from a foreign particle on the pericle inner surface is always received by at least one of the three photoelectric converters. Accordingly, to determine the foreign particle size form the photoelectric signal levels, an evaluation criterion prescribed by the algebraic sum of the six signal levels may be used since the three photoelectric converters 128a to 128f are provided in this embodiment. Alternatively, an evaluation criterion prescribed by the algebraic sum of the signal levels of the photoelectric converters (128d, 128e and 128f in this case) of the light receiving system having the larger angle to the pericle surface may be used.

The following is an example of a process of obtaining the constants $\alpha$, $\beta$ and $\gamma$ used with the algorism A mentioned above.

First, an inspection tool is provided in which a fine particle (a truly round bead or the like) used as a standard of foreign particles is blown and attached to a pericle surface. Foreign particle inspection is conducted with the apparatus shown in FIG. 7 by employing this inspection tool. While the standard particle having a known particle size is being irradiated with the beam S1, the levels of the signals VA to VF output from the photoelectric converters 128a to 128f and amplified are measured. The values of $\alpha$, $\beta$ and $\gamma$ are obtained from the measured values by $\alpha = (VA/VD) \cdot K\alpha$, $\beta = (VB/VE) \cdot K\beta$, and $\alpha = (VC/VF) \cdot K\gamma$. $K\alpha$, $K\beta$ and $K\gamma$ are constants which are set to satisfy $K\alpha > 1$, $K\beta < 1$ and $K\gamma > 1$ in consideration of the margin relating to the direction of each inequality sign of the algorism A.

With respect to this third embodiment, a modification using a slit-like illumination light and one-dimensional linear sensors is also possible. An example of such a modified construction is illustrated as a fourth example in FIG. 10.

Figure 10:
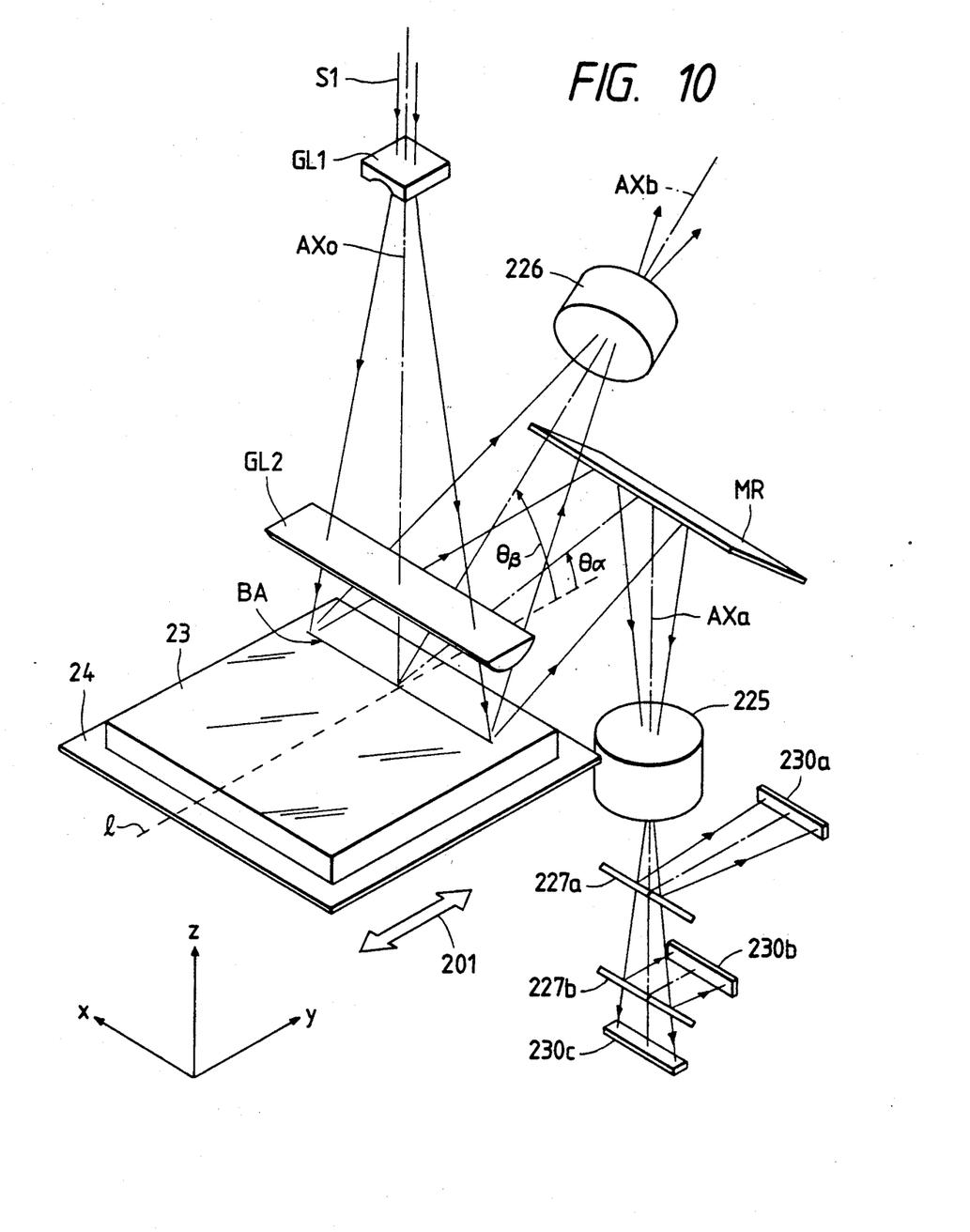
FIG. 10 is a perspective view of the construction of an apparatus in accordance with a fourth embodiment of the present invention.

Collimated multiple-color light S1 is expanded in the x-direction by a cylindrical concave lens GL1 and is condensed into a one-dimensionally elongated spot BA by a cylindrical convex lens GL2 having a base line extending in the x-direction. A reticle 24 on which a pericle 23 is mounted is one-dimensionally scanned in the y-direction, as indicated by an arrow 201. The spot BA has a length long enough to substantially cover the width of the whole surface of the pericle 23 in the x-direction. The width of the spot BA in the y-direction can be changed according to the desired fineness of the map (e.g., 1 mm). An optical axis AXo of the illumination optical system of the illumination light S1 is perpendicular or approximately perpendicular to the surface of the pericle 23.

The cylindrical lens GL2 may be replaced with an ordinary spherical lens system. Preferably, in such a case, the focal point of the spherical lens system on the light source side coincides with a virtual beam divergent point of the cylindrical lens GL1, and the pericle is adjusted to the focal point plane on the image side.

A line 1 extending in the y-direction on the pericle surface passes through the center of the spot BA and is perpendicular or approximately perpendicular to the spot BA. An optical axis AXa of the first light receiving system is reflexed by a mirror MR and is inclined relative to the line 1 in the z-direction by an angle $\theta a$ ($\theta a = 90° - \theta a$). An optical axis AXb of the second light receiving system is inclined relative to the line 1 in the z-direction by an angle $\theta \beta [(\theta \beta = 90° - \theta b)$.

A condenser lens 225 images a dark field image of the spot BA on three one-dimensional linear sensors 230a, 230b and 230c through dichroic mirrors 227a and 227b. Similarly, a condenser lens 226 images a dark field image of the spot BA on the three one-dimensional linear sensors (not shown in FIG. 10) through dichroic mirrors 227d and 227e which are the same as the corresponding mirrors shown in FIG. 7.

The size of pericles popularly used at present is substantially smaller than the size (5 or 6 inches) of reticles for reduction projection exposure. Accordingly, even if the length of the spot BA in the x-direction (the effective width of the pericle) is about 15 cm at the maximum, 200 arrays of one-dimensional linear array sensors will suffice in the case where the detection resolution is 1 mm square.

In the case of this arrangement, the inspection process may be such that the reticle is moved in the y-direction at a generally constant speed, one-dimensional signals are read from the respective one-dimensional linear sensors generally simultaneously each time the reticle is moved by 1 mm, and the ratio of the quantities of received light are obtained with respect to each pixel by using the same circuit as that shown in FIG. 8.

Figure 11:
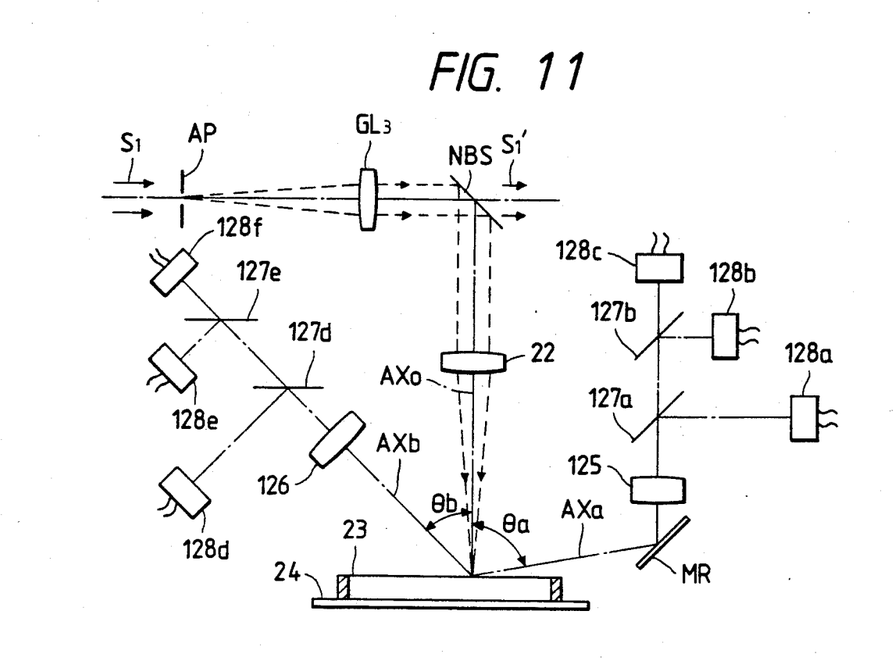
FIG. 11 is a diagram of the construction of an example of modification of the fourth embodiment.

FIG. 11 shows an example of modification of the fourth embodiment. Components having the same functions as those shown in FIG. 7 are indicated by the same reference characters.

The optical axis AXa of the first light receiving system is disposed to view the beam spot from the right-hand side of FIG. 11 at an angle $\theta a$ while the optical axis AXb of the second light receiving system is disposed to view the beam spot from the left-hand side of FIG. 11 at an angle $\theta b$. If the first and second light receiving systems are disposed on different sides with respect to the optical axis AXo of the illumination light S1, the two light receiving systems can be disposed very easily while maintaining the accuracy with which the surface on which a foreign particle is attached is determined.

An illumination field aperture AP is irradiated with the illumination light S1 at a uniform intensity. The illumination light S1 passing through the aperture AP is incident upon a condenser lens 22 through a lens system GL3 and a beam splitter NBS. The lens 22 forms an image of the aperture AP on the pericle. A part S1' of the illumination light passing through the beam splitter NBS is incident upon a reference light receiving system for monitoring fluctuations in the intensity of the light source and changes in the wavelength distribution. The reference light receiving system has the same spectral characteristics as the first and second light receiving systems and serves to constantly measure the intensity of the illumination light S1' with respect to particular wavelength ranges (e.g., three ranges of 600 to 700 nm, 700 to 800 nm and 800 to 900 nm).

Figure 12:
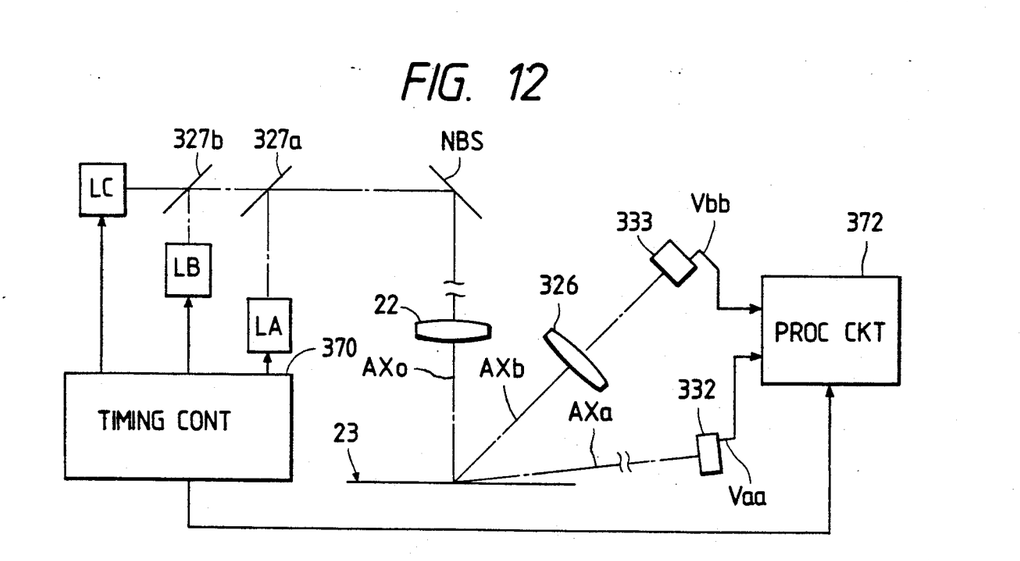
FIG. 12 is a diagram of the construction of an apparatus in accordance with a fifth embodiment of the present invention.

FIG. 12 shows the construction of an inspection apparatus in accordance with a fifth embodiment of the present invention. In this embodiment, the system for supplying pericle illumination light is devised unlike those of the above-described embodiments; spectroscopic elements including the dichroic mirrors are removed from the first and second light receiving systems while a single photoelectric converters is provided for each light receiving system.

Each of light sources LA, LB and LC is formed of a light emitting diode, a semiconductor laser or the like. These light sources emit light having different ranges of wavelengths according to the spectral characteristics of dichroic mirrors 327a and 327b (same as the mirrors 127a and 127b shown in FIG. 7). The illumination light from each of the three light sources travels along a common optical axis AXo, is reflected by a beam splitter NBS, and is condensed on a pericle by a condenser lens 22. First and second light receiving systems have high-speed response type photoelectric converters (photomultipliers or the like) 332 and 333. Photoelectric signals Vaa and Vbb output from these photoelectric converters are input into a processing circuit 372. The processing circuit 372 incorporates a divider for calculating the ratio (Vaa/Vbb) of the two photoelectric signals, an A/D converter which has a sample and hold circuit and which converts the ratio into digital values, a processor, a memory and so on.

The these light sources LA, LB and LC are controlled by a timing control circuit to selectively emit pulses of light at a high speed. A signal indicating the emission timing is sent to the processing circuit 372. In this arrangement, the light sources LA, LB and LC successively emit pulses of light when, for example, an optical axis AXo is moved to a map coordinate position on the pericle. The times for pulse emission are determined with lag times provided therebetween to avoid overlapping.

Each time one pulse of light is emitted, the processing circuit 372 uses the sample and hold function to successively stored the value of the output from the A/D converter in designated addresses of the memory. That is, the value Sa of the ratio (Vaa/Vbb) obtained when one area (e.g., 1 mm square) on the map is irradiated with a pulse of light from the light source LA, the value Sb of the ratio obtained when the same area is irradiated with a pulse of light from the light source LB, and the value Sc of the ratio obtained when the same area is irradiated with a pulse of light from the light source LC are stored in designated addresses of the memory. When the irradiated region is shifted to an adjacent area, the three light sources LA, LB, and LC are made to successively emit pulses of light again in the same manner.

After the measurement has been completed with respect to all designated regions on the pericle, inspection (evaluation) is conducted by the same procedure as that shown in FIG. 9B.

This embodiment requires the operation of making the three light sources successively emit light in different wavelength ranges, and may therefore increase the inspection time in comparison with the above-described embodiments. However, this embodiment has an advantage in that the construction of the light receiving systems can be markedly simplified and that the scale of the processing circuit can be reduced.

The present invention includes some other modifications of the above-described embodiments as described below.

As illumination light, light of a mercury discharge lamp containing a plurality of line spectra or light formed by composing light from a plurality of light emitting diodes (or semiconductor lasers) having different central wavelengths can be utilized. In a case of a system in which the pericle surface is scanned with a spot of illumination light by using a polygon mirror, a galvano mirror or the like, there is a possibility of the angle of incidence of the illumination beam on the pericle being changed according to the one-dimensional scanning position. Ordinarily, in this type of system, a lens system or the like for receiving scattered light is fixed to enable the whole of the one-dimensional scanning locus to be viewed in a particular spatial direction. The incident angle is therefore changed according to the scanning position of the spot, and the received light level is thereby changed. It is therefore preferable to provide a circuit for changing the level of the signal output from each photoelectric element of the light receiving systems or changing the slice level or the like for determining whether or not a foreign particle exists.

The dichroic mirrors provided as wavelength selecting elements used for the scattered light receiving systems may be replaced with other types of elements such as color filters or prisms (dispersion elements). In a case where a prisms are used, the spectral distribution of incident scattered light may be photoelectrically detected to determine the difference between the distribution of a spectrum of a foreign particle located on the outer surface of the pericle and the distribution of a spectrum of a foreign particle located on the inner surface of the pericle. However, since the intensity of scattered light from a foreign particle obtained by the spectroscopic effect of a prism is small, it is difficult to maintain the desired S/N ratio at the time of photoelectric conversion.

As described above with respect to the principle of the present invention, the intensity of scattered light from a foreign particle on the inner surface of the pericle peaks at the particular wavelength $\lambda m$, and is markedly reduced in wavelength ranges (between $\lambda m$ and $\lambda m$ 1, and between $\lambda m$ and $\lambda m - 1$) about this wavelength.

A type of optical system may therefore be adopted in which first illumination light having a band width of about 100 nm about the particular wavelength $\lambda m$ and second illumination light having a band width of about 100 nm spaced apart from the central wavelength $\lambda m$ of the first illumination light by several nanometers on the long wavelength side or short wavelength side are produced by separate light sources or one light source to be incident upon the same region on the pericle. In this case, a dichroic mirror for separating the first and second illumination lights is provided in each light receiving system, the relationship between the levels of signals from two photoelectric detection means is evaluated.

Accordingly, if the particular wavelength is about 565 nm and if a white light source such as a halogen lamp is sued, the pericle is irradiated with only light having a wavelength range of, for example, 500 to 700 nm separated by filtering from the light of the halogen lamp, and the sensitivity distribution of the first receiving is set to 500 to 600 nm while the sensitivity distribution of the second light receiving system is set to 600 to 700 nm.

Further, as described above with respect to the principle of the invention, the particular wavelength $\lambda m$ of scattered light from a foreign particle on the inner surface of the pericle depends upon the thickness d and the refractive index n of the pericle in accordance with equation (4). The particular wavelength may therefore be previously calculated by equation (4) with respect to pericles having different thicknesses and refractive indexes, and the selected wavelengths may be optimized for each pericle by suitably changing the angles θa and θb of the two light receiving system of changing the dichroic mirrors, thereby making it possible to discriminate the obverse or reverse surface with respect to various pericles.

What is claimed is:

1. An apparatus for inspecting surfaces of a flat transparent object, comprising:
    means for directing multiple-color light having an intensity distribution through a predetermined wavelength range to one of the surfaces of the flat object to illuminate same;
    detection means for detecting scattered light produced by a defect existing on one of the surfaces of the flat object with respect to a plurality of different wavelength ranges, and for producing a plurality of outputs corresponding to the intensities of scattered light of the plurality of wavelength ranges; and
    means for discriminating the surface of the flat object on which the defect exists based on the comparison between the plurality of outputs from said detection means.

2. An apparatus according to claim 1, wherein said detection means includes wavelength selection means for separating the scattered light with respect to the particular wavelength ranges.

3. An apparatus according to claim 2, wherein said detection means includes a plurality of photoelectric detectors for receiving respective lights separated by said wavelength selection means.

4. An apparatus for inspecting surfaces of a flat transparent object, comprising:
    irradiation means for directing multiple-color light having an intensity distribution through a predetermined wavelength range to one of the surfaces of the flat object to illuminate same;
    first detection means for detecting the quantities of multiple-color light from said illumination means with respect to a plurality of wavelength ranges and for producing corresponding outputs;
    second detection means for detecting the quantities of scattered light produced by a defect existing on one of the surfaces of the flat object with respect to a plurality of different wavelength ranges generally equal to the wavelength ranges with which said first detection means effects the detection, and for producing corresponding outputs; and
    comparison means for comparing the outputs from said first and second detection means with respect to the plurality of wavelength ranges.

5. An apparatus according to claim 4, further comprising means for discriminating in response to said comparison means the surface of the flat object on which the defect exists.

6. An apparatus according to claim 4, wherein said first detection means includes first spectroscopic means for separating multiple-color from said irradiation means with respect to the plurality of wavelength ranges, and a plurality of detectors for detecting the quantities of light with respect to the plurality of wavelength ranges with which the multiple-color light is separated by said first spectroscopic means.

7. An apparatus according to claim 6, wherein said second detection means includes second spectroscopic means for separating the scattered light produced by the defect existing on the surface of that flat object with respect to a plurality of wavelength ranges generally equal to the wavelength ranges with which the multiple-color light is separated by said first spectroscopic means, and a plurality of detectors for detecting the quantities of light with respect to the plurality of wavelength ranges with which the scattered light is separated by said second spectroscopic means.

8. An apparatus according to claim 4, wherein said comparison means obtains the ratio of the output from said first detection means and the output from said second detection means with respect to the plurality of wavelength ranges.

9. An apparatus according to claim 8, further comprising means for discriminating the surface of the flat object on which the defect exists by comparing the ratios obtained by said comparison means between different wavelength ranges.

10. An apparatus for inspecting surfaces of a flat transparent object, comprising:
    irradiation means for directing multiple-color light having an intensity distribution through a predetermined wavelength range to one of the surfaces of the flat object to illuminate same;
    a first light receiving system for receiving scattered light produced by a defect existing on one of the surfaces of the flat object in a direction at a predetermined angle to the surface of the flat object;
    a second light receiving system for receiving the scattered light in a direction at a angle to the surface of the flat object different from the angle at which said first light receiving system receives the scattered light;
    first detection means for detecting the quantity of scattered light received by said first light receiving system with respect to wavelength ranges according to predetermined spectral characteristics, and for outputting corresponding outputs;
    second detection means for detecting the quantity of scattered light received by said second light receiving system with respect to wavelength ranges according to substantially the same spectral characteristics as said first detection means; and
    comparison means for obtaining the ratio of the output from said first detection means and the output from said second detection means with respect to the plurality of wavelength ranges.

11. An apparatus according to claim 10, further comprising means for discriminating the surfaces of the flat object on which the defect exists based on the relationship between the ratios obtained by said comparison means.

12. An apparatus according to claim 10, wherein said irradiation means includes a single light source capable of supplying light having a continuous broad wavelength range or light having a plurality of discrete lime spectra.

13. An apparatus according to claim 10, wherein said irradiation means includes a plurality of light sources capable of supplying lights having different central wavelengths, and means for combining the lights from said plurality of light sources on a common optical axis.

14. An apparatus according to claim 10, wherein each of said first and second detection means includes a wavelength selecting element for separating the scattered light with respect to the wavelength ranges, and a plurality of photoelectric conversion elements for independently receiving the quantities of light of the respective wavelength ranges separated by said wavelength selecting means.

* * * * *